United States Patent
Bornzin et al.

(10) Patent No.: US 6,904,321 B1
(45) Date of Patent: *Jun. 7, 2005

(54) SYSTEM AND METHOD OF IDENTIFYING FUSION FOR DUAL-CHAMBER AUTOMATIC CAPTURE STIMULATION DEVICE

(75) Inventors: Gene A. Bornzin, Simi Valley, CA (US); Joseph J. Florio, La Canada, CA (US); Laurence S. Sloman, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 401 days.

This patent is subject to a terminal disclaimer.

(21) Appl. No.: 10/208,169

(22) Filed: Jul. 29, 2002

Related U.S. Application Data

(63) Continuation of application No. 09/630,771, filed on Aug. 2, 2000, now Pat. No. 6,456,881.

(51) Int. Cl.$^7$ .............................................. A61N 1/36
(52) U.S. Cl. ..................................................... 607/27
(58) Field of Search ...................................... 607/2–30

(56) References Cited

U.S. PATENT DOCUMENTS

| | | | |
|---|---|---|---|
| 4,686,988 A | 8/1987 | Sholder ................. | 128/419 PG |
| 4,708,142 A | 11/1987 | DeCote, Jr. ............ | 128/419 PT |
| 4,712,555 A | 12/1987 | Thornander et al. .. | 128/419 PG |
| 4,729,376 A | 3/1988 | DeCote, Jr. ............ | 128/419 PT |
| 4,878,497 A | 11/1989 | Callaghan et al. .... | 128/419 PG |
| 4,940,052 A | 7/1990 | Mann et al. ........... | 128/419 PG |
| 4,944,298 A | 7/1990 | Sholder ................. | 128/419 PG |
| 4,955,376 A | 9/1990 | Callaghan et al. .... | 128/419 PG |
| 4,969,460 A | 11/1990 | Callaghan et al. .... | 128/419 PG |
| 4,969,461 A | 11/1990 | Callaghan et al. .... | 128/419 PG |
| 4,969,462 A | 11/1990 | Callaghan et al. .... | 128/419 PG |
| 4,969,464 A | 11/1990 | Callaghan et al. .... | 128/419 PG |
| 4,969,467 A | 11/1990 | Callaghan et al. .... | 128/419 PG |
| 5,334,220 A | 8/1994 | Sholder ......................... | 607/9 |
| 5,350,410 A | 9/1994 | Kleks et al. ................... | 607/28 |
| 5,466,254 A | 11/1995 | Helland ....................... | 607/123 |
| 5,573,550 A | 11/1996 | Zadeh et al. ................. | 607/28 |
| 5,685,315 A | 11/1997 | McClure et al. ............. | 128/708 |
| 5,713,930 A | 2/1998 | van der Veen et al. ....... | 607/25 |
| 5,766,229 A | 6/1998 | Bornzin ....................... | 607/28 |
| 6,038,474 A | 3/2000 | Zhu et al. ...................... | 607/9 |
| 6,324,427 B1 | 11/2001 | Florio ........................... | 607/28 |
| 6,339,723 B1 | 1/2002 | Sloman ....................... | 607/28 |
| 6,788,971 B1 * | 9/2004 | Sloman et al. ................ | 607/28 |

OTHER PUBLICATIONS

Bornzin, Gene, et al., Dual–Chamber AutoCapture System Algorithm that Saves Pacing Energy and Avoids Fusion in Patients with Intact Conduction, HeartWeb, vol. 2, No. 1, Article No. 96110024, pp 1–6 (Nov. 1996).

(Continued)

*Primary Examiner*—Scott M. Getzow

(57) ABSTRACT

A multi-chamber stimulation device and associated method reliably and automatically distinguish fusion from loss of capture during ventricular stimulation. The stimulation device provides immediate and accurate fusion detection when a loss of capture is suspected in the ventricles without delivering back-up stimulation pulses. To achieve this objective, the far-field signal present in the atrial channel is examined for evidence of a far-field R-wave whenever the ventricular channel detects a loss of capture. If a far-field R-wave is present, fusion is confirmed, and a far-field R-wave is absent, loss of capture is confirmed. Additionally, the stimulation device inhibits unnecessary back-up stimulation and threshold tests when fusion occurs, and provides appropriate adjustment of stimulation parameters based on confirmed fusion detection such that fusion re-occurrence is minimized.

22 Claims, 4 Drawing Sheets

OTHER PUBLICATIONS

Florio, Joseph, et al., "Preliminary Results of a New Single Chamber Pacemaker with Autocapture Function", European Journal of Cardiac Pacing and Electrophysiology, vol. 4, No. 2, Abstract No. 211, pp.: 50 (Jun. 1994).

Bornzin, Gene A. PhD, et al., "Dual Chamber Autocapture Algorithm that Saves Pacing Energy and Avoids Fusion in Patients with Intact Conduction", European Journal of Cardiac Pacing and Electrophysiology, vol. 6, No. 1, Supplement 5, Abstract No. 786 84/6, pp.: 197 (Jun. 1996).

Sholder, Jason, et al., "Autocapture–Future Directions", European Journal of Cardiac Pacing and Electrophysiology, vol. 6, No. 1, Supplement 5, Abstract No. 641 33/6, pp.: unknown (Jun. 1996).

Florio, Joseph, et al., "Investigation of Evoked Response Sensing Configurations for Autocapture Using a Pacing System With An Onboard A/D Converter", European Journal of Cardiac Pacing and Electrophysiology, vol. 6, No. 1, Supplement 5, Abstract No. 632 29/PW6, pp.: 159 (Jun. 1996).

Jalali, Laleh, BS, et al., "Atrial Evoked Response and Polarization Evaluated in a Pacing System with an Onboard A/D Converter", PACE, vol. 20, Part II, Abstract No. 188 pp.: 1096 (Apr. 1997).

Jalali, L., et al., Atrial Evoked Response and Polarization Evaluated in a Pacing System with an Onboard A/D Converter, EUROPACE, pp.: 653 (Jun. 8–11, 1997).

Kerry Bradley, MS, et al., An Atrial Autothreshold Algorithm Using the Atrial Evoked Response, PACE, vol. 22, Part II, Abstract 606, pp.: 851(Apr. 1999).

Kerry Bradley, MS, et al., An Atrial Autothreshold Algorithm Using the Atrial Evoked Response, PACE, vol. 22, Part II, Abstract 017, pp.: A5 (Jun. 1999).

Florio, Joseph, et al., "Verifying Capture in A Parallel Configuration Bi–Ventricular Pacing System", PACE, vol. 23, Part II, Abstract No. 679, pp.: 722 (Apr. 2000).

Florio, Joseph, et al., "Verifying Capture in a Parallel Configuration Bi–Ventricular Pacing System", EUROPACE Supplements, vol. 1, Supplement D, Abstract No. 88/6, pp.: D96 (Jul. 2000).

Pianca, Anne M., BSME, et al., "Left Ventricular AutoCapture™", EUROPACE Supplements, vol. 1, Supplement D, Abstract No. 96PW/19, pp.: D110 (Jul. 2000).

* cited by examiner

SYSTEM AND METHOD OF IDENTIFYING FUSION FOR DUAL-CHAMBER AUTOMATIC CAPTURE STIMULATION DEVICE

CROSS-REFERENCE TO RELATED APPLICATIONS

This application is a continuation of U.S. patent application Ser. No. 09/630,771, filed Aug. 2, 2000 now U.S. Pat. No. 6,456,881.

FIELD OF THE INVENTION

The present invention generally relates to a programmable cardiac stimulation device for automatically monitoring capture, following the delivery of a stimulation pulse More specifically, the stimulation device has the ability to distinguish fusion from a loss of capture during dual-chamber or multi-chamber stimulation.

BACKGROUND OF THE INVENTION

In healthy human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system, causing a depolarization known as an R-wave and the resulting ventricular chamber contractions. Disruption of this natural pacemaking and conduction system as a result of aging or disease can be successfully treated by artificial cardiac pacing using implantable cardiac pacing devices, including pacemakers and implantable defibrillators, which deliver rhythmic electrical pulses or anti-arrhythmia therapies to the heart at a desired energy and rate. One or more heart chambers may be electrically paced depending on the location and severity of the conduction disorder.

Modern pacemakers and implantable defibrillators possess numerous operating parameters, such as pacing pulse energy, base pacing rate, sensing threshold, pacing mode, etc., that must be programmed by the physician to satisfy individual patient need. In practice, this programming process can be time consuming and complicated. One goal of pacemaker manufacturers, therefore, has been to fully automate pacemaker function in order to minimize the complexity of programming operations and to maximize the safety and effectiveness of the cardiac pacing device.

One basic function of the pacemaker is to deliver a pacing pulse of sufficient energy to depolarize the cardiac tissue causing a contraction, a condition commonly known as "capture." Automating this function continues to be a strong focus of development efforts by pacemaker manufacturers. A straightforward approach to ensure capture is to deliver a fixed high-energy pacing pulse. While this approach, used in early pacemakers is simple, it quickly depletes battery energy and can result in patient discomfort due to extraneous stimulation of surrounding skeletal muscle tissue.

Therefore, a goal which is strived for in the pacemaker industry is to deliver pacing pulses at, or slightly higher than the pacing "threshold." Pacing threshold is defined as the lowest pacing pulse energy at which capture occurs. By stimulating the heart chambers at or just above threshold, comfortable and effective cardiac pacing is provided without unnecessarily depleting battery energy. Pacing threshold, however, is extremely variable from patient-to-patient due to variations in electrode systems used, electrode positioning, physiological and anatomical variations of the heart itself and so on.

Therefore, at the time of device implant, the pacing threshold is determined by the physician who observes an ECG recording while pulse energy is decreased, either by decrementing the pulse amplitude or the pulse width, until capture disappears. The pacing pulse energy is then programmed to a setting equal to the lowest pulse energy at which capture still occurred (threshold) plus some safety margin to allow for small fluctuations in the threshold. Selection of this safety margin, however, can be arbitrary. Too low of a safety margin may result in loss of capture, a potentially fatal result for the patient. Too high of a safety margin will lead to premature battery depletion and potential patient discomfort.

Furthermore, pacing threshold will vary over time within a patient due to fibrotic encapsulation of the electrode that occurs during the first few weeks after surgery; fluctuations that may occur over the course of a day, with changes in medical therapy or disease state and so on. Hence, techniques for monitoring the cardiac activity following delivery of a pacing pulse have been incorporated in modern pacemakers in order to verify that capture has indeed occurred. If a loss of capture is detected by such "capture-verification" algorithms, a threshold test is performed by the cardiac pacing device in order to re-determine the pacing threshold and automatically adjust the pacing pulse energy. This approach, as embodied in the Pacesetter, Inc. AUTOCAPTURE™ Pacing System, improves the patient's comfort, reduces the necessity of unscheduled visits to the medical practitioner, and greatly increases the pacemaker's battery life by conserving the energy used to generate stimulation pulses.

A widely implemented technique for determining whether capture has occurred is monitoring the myocardial or intracardiac electrogram (EGM) received on the cardiac pacing and sensing electrodes. Heart activity is monitored by the pacemaker by keeping track of the stimulation pulses delivered to the heart and examining the EGM signals that are manifest concurrent with depolarization or contraction of muscle tissue (myocardial tissue) of the heart. The contraction of atrial muscle tissue is evidenced by generation of a P-wave, while the contraction of ventricular muscle tissue is evidenced by generation of an R-wave (sometimes referred to as the "QRS" complex). Through sampling and signal processing algorithms, the presence of an "evoked response" following a pacing pulse is determined The "evoked response" is the depolarization of the heart tissue in response to a stimulation pulse, in contrast to the "intrinsic response" which is the depolarization of the heart tissue in response to the heart's natural pacemaking function.

When capture occurs, the evoked response is an intracardiac P-wave or R-wave that indicates contraction of the respective cardiac tissue in response to the applied stimulation pulse. For example, using such an evoked response technique, if a stimulation pulse is applied to the ventricle (hereinafter referred to as a Vpulse), a response sensed by ventricular sensing circuits of the pacemaker immediately following application of the Vpulse is presumed to be an evoked response that evidences capture of the ventricles.

However, it is for several reasons very difficult to detect a true evoked response. One problem commonly encountered during capture verification is "fusion." Fusion occurs when a pacing pulse is delivered such that the evoked response occurs coincidentally with an intrinsic depolarization. The evoked signal may be absent or altered preventing correct capture detection by the pacemaker's capture detection algorithm. A loss of capture may be indicated when capture is in fact present, which is an undesirable situation that will cause the pacemaker to unnecessarily deliver a high-energy back-up pacing pulse and to invoke the threshold testing function in a chamber of the heart. Frequent delivery of back-up pacing pulses or execution of threshold tests defeats the purpose of the energy-saving features of AUTOCAPTURE™. If fusion continues during a threshold test, the pacing energy output may be driven to a maximum level, quickly depleting the battery energy.

The incidence of fusion can be particularly problematic in patients with intermittent or intact atrio-ventricular conduction being treated by dual-chamber pacing. In dual-chamber pacing, both atrial and ventricular activity are monitored. A P-wave detected in the atria is followed by an AV/PV interval, which is the desired delay between an atrial depolarization and a ventricular depolarization. If an intrinsic R-wave is not detected prior to expiration of the AV/PV delay, a Vpulse is delivered to pace the ventricles. Since the AV conduction time may vary, an intrinsically conducted R-wave may occur at different times and therefore may occur approximately the same time that a ventricular pacing pulse is delivered. Furthermore, the AVIPV interval may be programmed inappropriately leading to increased likelihood of fusion events. Fusion masquerading, as loss of capture will cause the pacemaker to initiate frequent threshold tests and may drive the pacemaker to its maximum pacing output.

Rate variability, particularly in rate-responsive pacemakers, may further complicate timing sequences. In rate-responsive pacemakers, the pacing interval automatically shortens in response to increased metabolic demand. However, the AV interval may not be shortened accordingly resulting in increased likelihood of fusion.

To address the problem of fusion, techniques have been proposed to shorten the pacing interval subsequent to a loss of capture. By pacing earlier, fusion is less likely to occur during future pacing cycles. Reference is made for example to U.S. Pat. Nos. 4,969,462 and 4,969,467 to Callaghan et al.

In order to verify that fusion has occurred, a method has been proposed to make use of the physiological refractory time of cardiac tissue. Reference is made for example to U.S. Pat. No. 4,955,376 to Callaghan et al. This method takes advantage of the fact that once cardiac tissue has been depolarized, it cannot be depolarized again until the ion flow that has occurred across the cardiac cell membrane during the first depolarization has returned to the resting state. This time period is known as refractory. If a high-energy back-up pacing pulse is delivered during the physiologic refractory period, no depolarization will result. Therefore, if a high-energy pacing pulse delivered soon after a loss of capture does not elicit an evoked response, the loss of capture was likely to have been a fusion event that was misdetected. On the other hand, if an evoked response is detected following the back-up pacing pulse, then the loss of capture detection is accurate. The back-up pacing pulse is necessary for the implementation of this method, and is followed by an automatic threshold test. However, the delivery of a high-energy pacing pulse for verifying the occurrence of fusion uses precious battery life without direct therapeutic benefit.

Zhu et al. provide a method in U.S. Pat. No. 6,038,474 for avoiding fusion during auto-capture regimes by delivering a "pre-look" pacing pulse in order to determine if a fusion event is mistaken for a loss of capture. This approach requires the delivery of an additional pulse in order to avoid or verify fusion. Delivery of this additional pacing pulse does not fully conform to the overall energy-savings intent of AUTOCAPTURE™ regimes.

The difficulty heretofore, is the inability to reliably detect when fusion occurs, without expending energy on back-up or pre-look pacing pulses and automatic threshold tests. The difficulty in detecting fusion arises from polarization effects on the electrodes used for both pacing and sensing, and the alteration of the evoked response during fusion, making it undetectable by the normal capture verification regimes. Hence, fusion is misinterpreted as a loss of capture by the ventricular channel.

However, a signal associated with the ventricular R-wave is also detectable on the atrial channel, known as a "far-field" R-wave, or FFR. FFR signals are generally ignored, and oftentimes avoided, on the atrial channel by applying blanking and refractory intervals following the delivery of a Vpulse because far-field signals might otherwise be inaccurately interpreted as atrial events. However, detection of a FFR on the atrial channel during fusion would provide a way of determining that fusion has occurred without delivering additional pacing pulses. The FFR signal resulting from a normal R-wave and during a fusion event is similar in morphology. Therefore, detection of a FFR on the atrial channel when loss of capture occurs on the ventricular channel would be a useful means for detecting fusion.

It would thus be desirable, particularly in dual-chamber pacemakers, to provide a system and method for accurately detecting fusion events. Furthermore, it would be desirable to detect fusion without requiring delivery of additional pacing pulses, particularly high-energy pacing pulses.

SUMMARY OF THE INVENTION

The present invention addresses these and other problems by providing a multi-chamber stimulation device that reliably and automatically distinguishes fusion from loss of capture during ventricular stimulation.

One feature of the present invention is to provide immediate and accurate fusion detection when a loss of capture is suspected in the ventricles without delivering back-up stimulation pulses. To achieve this objective, the far-field signal present in the atrial channel is examined for evidence of a FFR (far-field R-wave) whenever the ventricular channel detects a loss of capture. If a FFR is present, fusion is confirmed. If a FFR is absent, loss of capture is confirmed.

An additional feature of the present invention is the inhibition of a back-up stimulation pulse upon fusion detection. A high-energy back-up stimulation pulse is normally generated by the ventricular channel when loss of capture is detected. By correctly distinguishing fusion from a loss of capture, back-up stimulation can be inhibited as well as the normally invoked threshold test. Hence, the present invention provides an important energy-savings feature.

Yet another feature of the present invention is the automatic adjustment of stimulation parameters whenever fusion is confirmed, so that fusion can be avoided on future paced beats or during future threshold tests. Thus, the present invention improves the performance of the pacemaker device by properly distinguishing fusion from loss of capture and responding appropriately to both situations.

Therefore, the present invention achieves several objectives, among which are the following: 1) accurate detection of fusion immediately upon its occurrence, without delivering additional stimulation pulses; 2) inhibition of unnecessary back-up stimulation and threshold tests when fusion occurs; and 3) appropriate adjustment of stimulation parameters based on confirmed fusion detection such that fusion recurrence is minimized.

BRIEF DESCRIPTION OF THE DRAWINGS

The above and further features, advantages and benefits of the present invention will be apparent upon consideration of the present description taken in conjunction with the accompanying drawings, in which.

DETAILED DESCRIPTION OF THE INVENTION

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout.

The present invention is directed at distinguishing fusion from loss of capture during ventricular AUTOCAPTURET™ regimes. When fusion is verified, back-up ventricular stimulation is inhibited and no threshold test is performed as would normally occur following a loss of capture detection. Furthermore, stimulation parameters may be automatically adjusted following fusion verification in order to prevent fusion from occurring on future paced beats. These methods are preferably implemented in a cardiac stimulation system including any one or more of an implantable pacemaker, a cardioverter, and/or a defibrillator device, and associated leads that provide electrical connection with the heart. The methods of the present invention are then carried out by the internal circuitry of the stimulation device. Prior to describing in detail the stimulation system and methods of the present invention, one embodiment of an implantable cardiac stimulation system will be briefly described now, and more completely described later.

Figure 1:
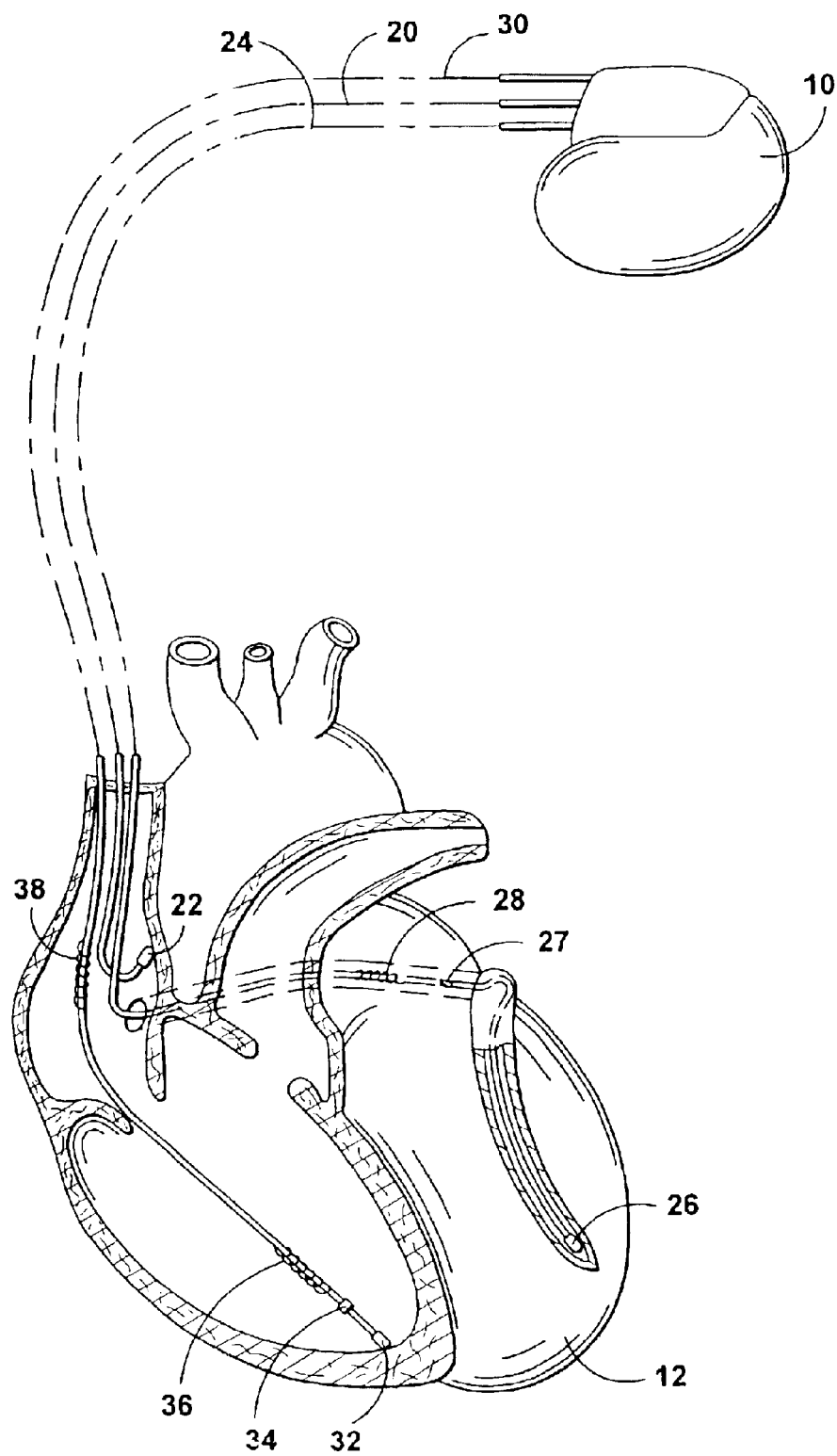
FIG. 1 is a simplified, partly cutaway view illustrating an implantable stimulation device of the present invention, in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular stimulation therapy using at least a left ventricular tip electrode 26, left atrial stimulation therapy using at least a left atrial ring electrode 27, and shocking therapy using at least a left atrial coil electrode 28. For a complete description of a coronary sinus lead, refer to U.S. patent application Ser. No. 09/457,277, titled "A Self-Anchoring, Steerable Coronary Sinus Lead" (Pianca et. al), and U.S. Pat. No. 5,466,254, titled "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the right ventricle coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of stimulation and shock therapy to the right ventricle.

Figure 2:
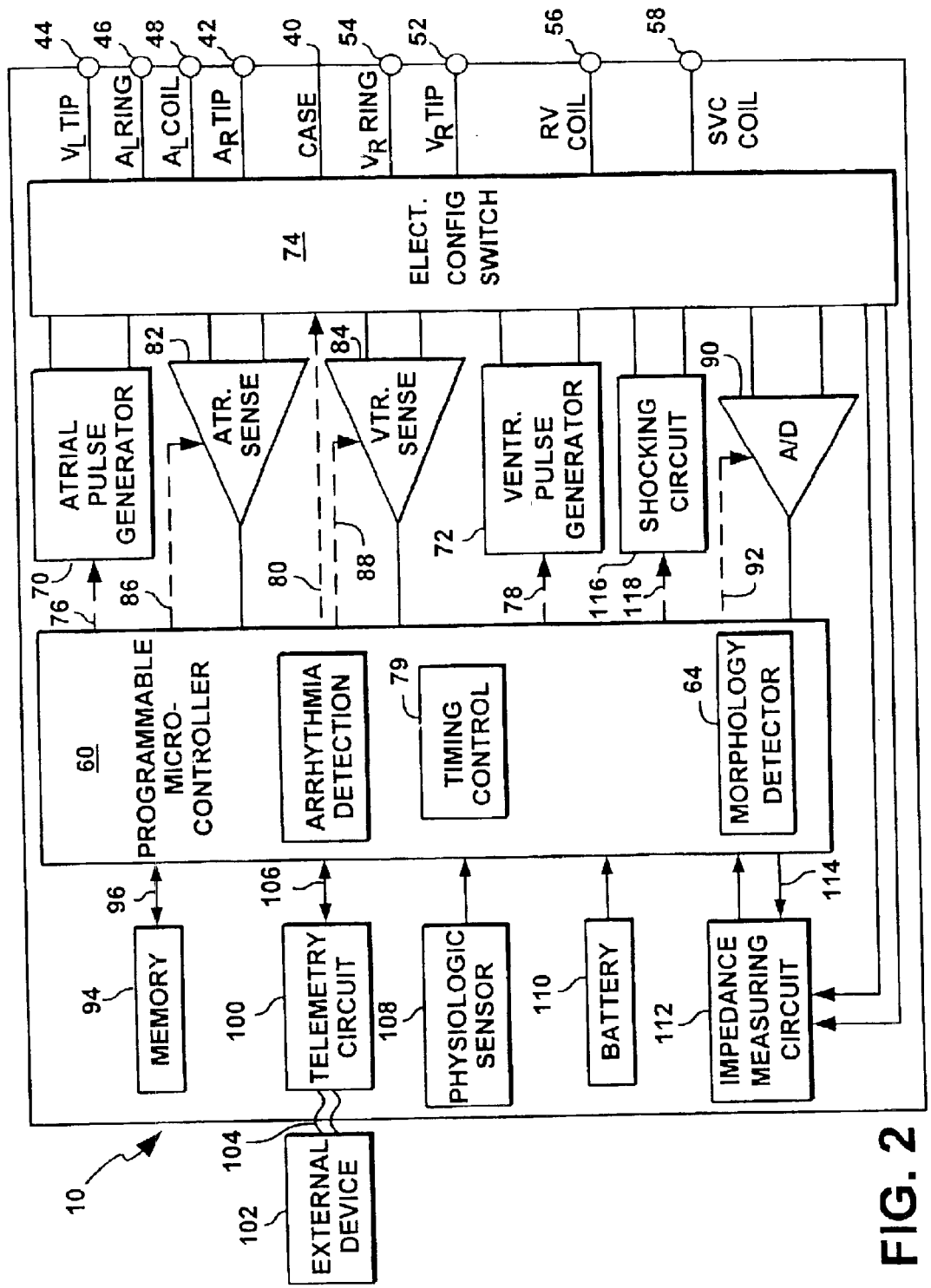
FIG. 2 is a functional block diagram of the multi-chamber implantable stimulation device of FIG. 1, illustrating the basic elements that provide cardioversion, defibrillation and stimulation in four chambers of the heart.

FIG. 2 illustrates a simplified block diagram of the multi-chamber implantable stimulation device 10, which is capable of treating both fast and slow arrhythmias with stimulation therapy, including stimulation, cardioversion, and defibrillation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and stimulation.

The stimulation device 10 is encased in a housing 40 which is often referred to as "can", "case" or "case electrode", and which may be programmably selected to act as the return electrode for all "unipolar" stimulation or sensing modes.

The stimulation device 10 generally includes an atrial channel, which includes atrial sensing circuitry 82 and an atrial pulse generator 70, and a ventricular channel, which includes ventricular sensing circuitry 84 and a ventricular pulse generator 72. The interpretation of sensed atrial and ventricular activity and coordination of stimulation, cardioversion, or defibrillation therapy delivery by the atrial and ventricular channels are controlled by a programmable microcontroller 60. Microcontroller 60 typically includes a microprocessor and memory such that operation codes can be performed based on programmable parameters, such as stimulation pulse amplitude, AV interval, sensitivity and so forth. Such programmable parameters may be selected by the physician using an external device 102 in communication with a telemetry circuit 100.

In this embodiment, the control program is comprised of multiple integrated program modules, with each module bearing responsibility for controlling one or more functions of the stimulation device 10. For example, one program module may control the delivery of stimulating pulses to the heart 12, while another may control the ventricular stimulation energy determination. In effect, each program module is a control program dedicated to a specific function or set of functions of the stimulation device 10.

Figure 3:
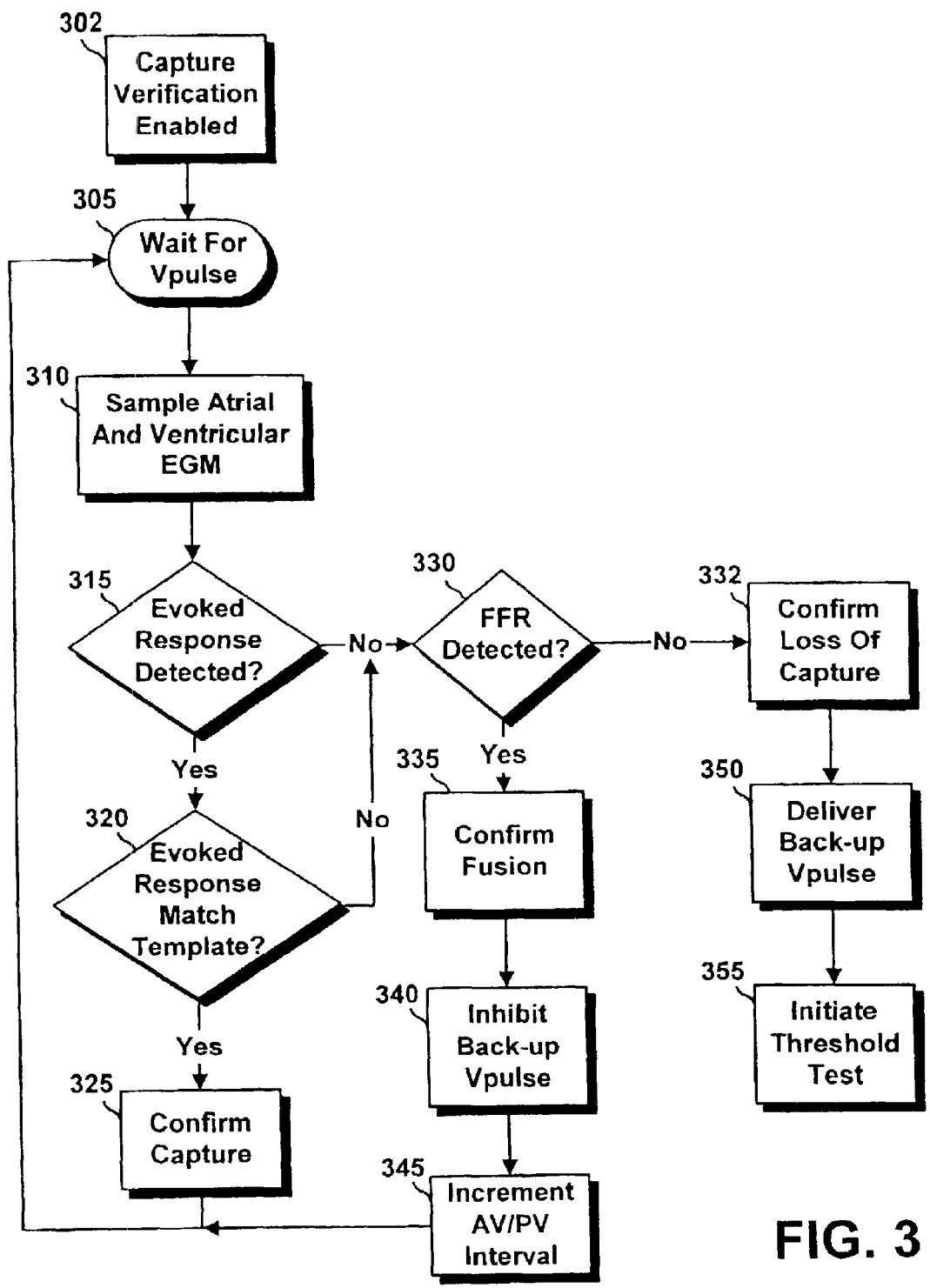
FIG. 3 is a flow chart describing an overview of the operation of one embodiment of the present invention used by the stimulation device of FIG. 2 for detecting fusion.

In particular, a program module is implemented by the stimulation device 10 to verify ventricular capture in accordance with the present invention. FIG. 3 is a flow diagram describing an overview of the operation and features of a method 300 for automatically distinguishing fusion from loss of capture during ventricular capture verification. In this flow chart the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Method 300 is implemented whenever microcontroller 60 performs capture verification in either or both the right and left ventricles. Ventricular capture verification may occur continuously during stimulation, i.e. on a beat-by-beat basis, or it may be triggered to occur on a periodic basis, such as hourly, daily, or otherwise. Preferably, the frequency with which capture verification is performed is controlled by programmable parameters set by the medical practitioner using. the external programming device 102. The appropriate testing frequency will vary from patient to patient and will depend on a number of physiologic and other factors. For example, if a patient is on a cardiac medication regime, the patient's ventricular capture threshold may fluctuate, thus requiring relatively frequent testing. Other factors may affect the anticipated frequency of fusion. For example, if the device is a rate-responsive pacemaker, which changes the ventricular stimulation rate in response to changes in metabolic demand, or if the patient's AV conduction time is variable due to disease or medication, the likelihood of a Vpulse being delivered coincidentally with an intrinsic depolarization may increase. In patients suspected of having increased likelihood of fusion, capture verification may be invoked more frequently such that the methods of the present invention may vigilantly detect and avoid fusion.

Once ventricular capture verification is enabled at step 302, method 300 waits for ventricular pulse generator 72 to deliver a ventricular stimulation pulse at step 305. During dual-chamber or multi-chamber stimulation, a Vpulse will be delivered if an R-wave is not sensed prior to the expiration of the AV or PV interval. Immediately after delivery of a Vpulse, atrial sensing circuit 82 begins sampling and storing the atrial EGM, and ventricular sensing circuit 84 begins sampling and storing the ventricular EGM. The ventricular EGM is sampled from the ventricular chamber in which stimulation is applied, which could be the left ventricle, the right ventricle or both. The sampling period extends for a pre-defined time following the Vpulse, e.g. 50 to 100 msec.

The ventricular signal may be sensed in either unipolar, bipolar or combipolar configurations. In the embodiment shown in FIG. 1, the right ventricle signal may be sensed in a unipolar configuration between a right ventricular tip electrode 32 and the pacemaker housing 40 or alternatively between a right ventricular ring electrode (not shown) and the pacemaker housing 40. The right ventricle signal may also be sensed in a bipolar configuration between right ventricular tip electrode 26 and a right ventricular ring electrode (not shown). Likewise, the left ventricle signal may be sensed in a unipolar configuration between left ventricular tip electrode 26 and the pacemaker housing 40 or between a left ventricular ring electrode (not shown) and the pacemaker housing 40. Alternatively, the left ventricular EGM may be sensed in a bipolar configuration between coronary sinus electrode 27 and left ventricular tip electrode 26. The electrode polarity used will depend on the system and electrodes implanted. In the preferred embodiment, the electrode polarity giving the best signal-to-noise ratio is selected by the physician at the time of implant or during an office visit.

Similarly, the atrial signal may be sensed in either unipolar, bipolar or combipolar configurations depending on the system and electrodes implanted. Either the right atrial EGM signal or the left atrial EGM signal may be used for successfully carrying out the methods of the present invention in detecting the FFR associated with capturing the right ventricle, the left ventricle, or both. In a preferred embodiment, the right atrial EGM is sensed between the RA tip electrode 22 and the pacemaker housing 40. Alternatively, the left atrial EGM is sensed between the coronary sinus ring electrode 27 and the pacemaker housing 40.

At decision step 315, microcontroller 60 determines if an evoked response is detected from the sampled ventricular signal. Various exemplary methods for sensing and detecting an evoked response to verify capture are described for example in U.S. Pat. No. 4,729,376 (Decote, Jr.); U.S. Pat. No. 4,708,142 (Decote, Jr.); U.S. Pat. No. 4,686,988 (Sholder); U.S. Pat. No. 5,766,229 (Bomzin), and U.S. Pat. No. 5350,410 (Mann et. al), all of which patents are hereby incorporated herein by reference.

If an evoked response is detected at decision step 315, it is compared to the characteristics of a typical evoked response. In a preferred embodiment, this comparison is based on an average morphology template determined by morphology detector 64 (FIG. 2). If the detected evoked response matches (e.g. it is approximately equal to) an evoked response template at step 320, capture is confirmed at step 325, and method 300 returns to step 305 to wait for the next Vpulse or until ventricular capture verification is disabled. Other methods of verifying detection of an evoked response could be employed such as amplitude comparison, event width comparison, slope comparison, etc.

If the detected evoked response does not match an average evoked response template (step 320), or if no evoked response was detected at all at decision step 315, microcontroller 60 examines the atrial sensed signal at decision step 330 to determine if a FFR signal was detected. One method for detecting a FFR has been described in detail in U.S. patent application Ser. No. 09/946,614, filed Dec. 14, 1999, entitled "System and Method for Ventricular Capture Using Far Field Evoked Response," incorporated herein by reference, and therefore a detailed description of FFR detection will not be made here.

Figure 4:
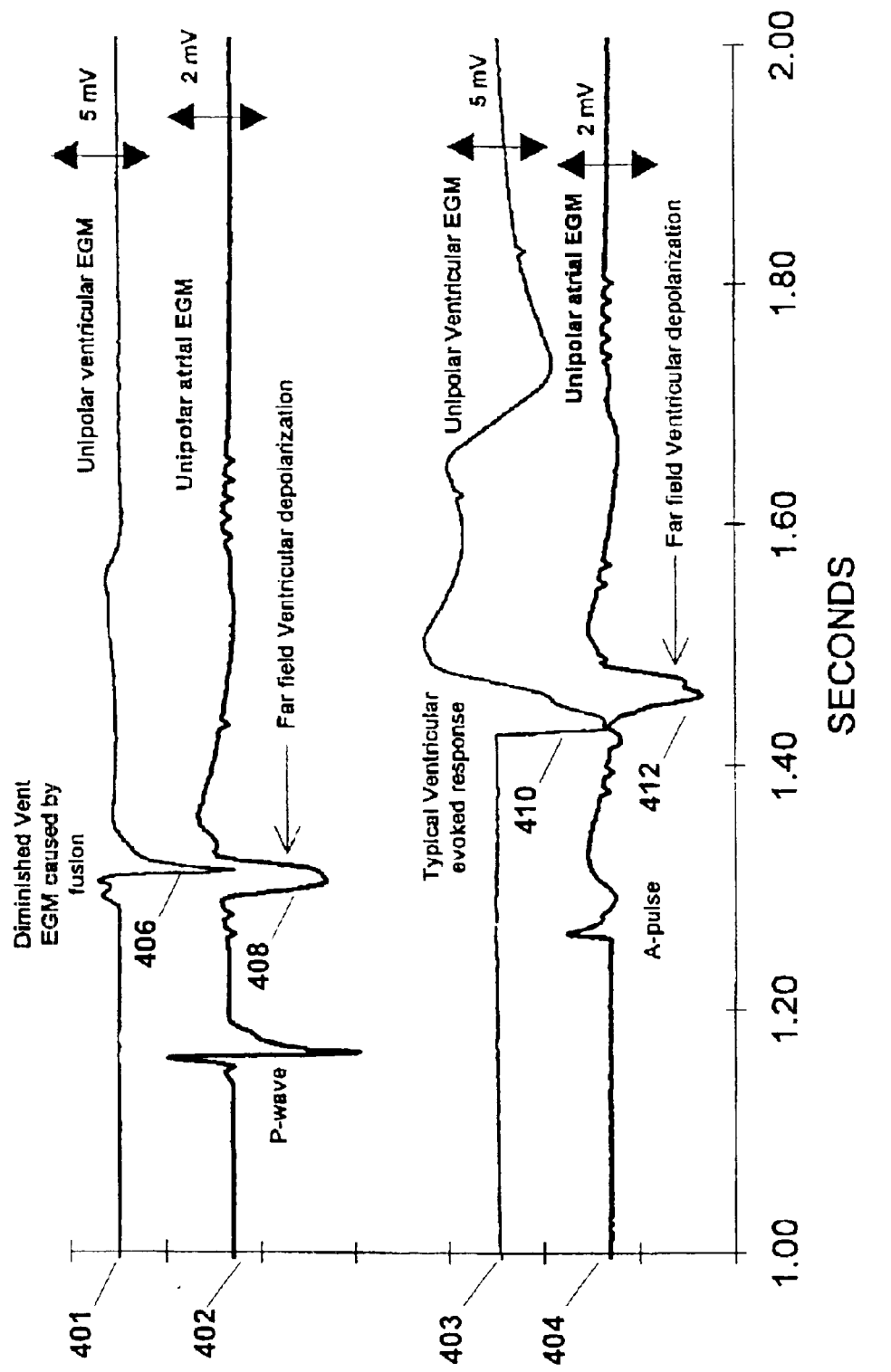
FIG. 4 is a graphical display of exemplary sensed signals of: 1) a fusion event showing a distorted R-wave on a ventricular EGM channel and its associated FFR on a simultaneous atrial EGM channel, and 2) a normal evoked response on a ventricular EGM channel and its associated FFR on a simultaneous atrial EGM channel.

The relevance of using FFR detection for verifying fusion is elucidated in FIG. 4. A ventricular EGM signal is shown during a fusion event in the upper trace 401. The evoked response signal 406 is distorted due to the concurrent delivery of the ventricular stimulation pulse with an intrinsic depolarization. The second trace 402 shows the simultaneously sampled atrial EGM signal. A FFR signal 408 is easily observed coinciding in time with the fusion event on the ventricular channel. This FFR signal 408 is substantially similar to the FFR signal 412 obtained when normal ventricular capture occurs as shown in the fourth trace 404. In the latter case, the FFR 412 coincides with an evoked response signal 410 on the ventricular EGM shown in the third trace 403. Notice that the event width and amplitude of the ventricular depolarizations 406 and 410 in traces 401 and 403 are substantially different. The diminished evoked response signal 406 due to fusion may go undetected by normal capture verification methods, and therefore be mistaken for a loss of capture. By sensing for the FFR whenever loss of capture is suspected on the ventricular channel, fusion can be readily detected.

Thus, referring again to FIG. 3, if no FFR is detected at step 330, then loss of capture can be confirmed at step 332. Microcontroller 60 responds by triggering a high-energy back-up stimulation pulse at step 350. This back-up stimulation pulse restores ventricular activity by capturing the ventricle(s) using a high-energy stimulation pulse until the capture threshold can be redetermined and ventricular stimulation energy adjusted. Hence, at step 355, the method 300 initiates a threshold test in the ventricular chamber in which loss of capture has been confirmed. Methods for performing threshold tests are commonly known in the art and will not be described in detail here. For a detailed description of a threshold test reference is made to U.S. Pat. No 5,766,229 to Bornzin, which is incorporated herein by reference.

If, at step 330, a FFR is detected, then fusion can be confirmed at step 335. The loss of capture detected by the ventricular channel is erroneous, hence, the loss of capture is reclassified as fusion and, at step 340, microcontroller 60 inhibits the delivery of a high-energy back-up stimulation pulse that would normally be delivered upon loss of capture. Since loss of capture is not verified, a threshold test need not be performed.

Rather, in the preferred embodiment, stimulation parameters are adjusted such that the likelihood of fusion on future stimulation cycles is minimized. As shown in FIG. 3, microcontroller 60 increments the AV and the PV intervals at step 345. Preferably, the AV and PV intervals are increased by a predefined, preferably programmable, amount of time, for example 100 msec. By extending the AV/PV intervals, the intrinsic conducted R-wave is allowed to occur and inhibit stimulation output. Thus, battery energy is saved.

Alternatively, other fusion avoidance techniques may be applied at step 345 once fusion has been confirmed. For example, a shorter stimulation rate or shortened AV and PV intervals would also effectively change the timing interval at which the Vpulse is delivered and reduce the likelihood of fusion. These adjustments result in predominate stimulation rather than stimulation inhibition, however, this may be preferable in selected patients, for example patients that benefit hemodynamically from a short AV or PV interval.

In another embodiment of the present invention, fusion detection as described in conjunction with FIG. 3 is also applied during the execution of threshold tests. If undetected fusion were to occur during a threshold test, the threshold result may be inappropriately high, or even reach the maximum output available due to the inability of the algorithm to verify capture at any given pulse energy. By verifying that fusion has not occurred whenever a test pulse results in a capture failure ensures confidence in the final threshold test result.

Having described the methods of the present invention in detail, one embodiment in which the present invention may operate will now be described in greater detail in conjunction with FIG. 2.

The housing 40, encasing the multi-chamber implantable stimulation device 10, includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and stimulation, the connector includes at least a right atrial tip terminal 42 adapted for connection to the atrial ($A_R$) tip electrode 22.

To achieve left chamber sensing, stimulation or shocking, the connector includes at least a left ventricular ($V_L$) tip terminal 44, a left atrial ($A_L$) ring terminal 46, and a left atrial ($A_L$) shocking terminal (coil) 48, which are adapted for connection to the left ventricular tip electrode 26, the left atrial tip electrode 27, and the left atrial coil electrode 28, respectively.

To support right chamber sensing, stimulation and/or shocking, the connector further includes a right ventricular ($V_R$) tip terminal 52, a right ventricular ($V_R$) ring terminal 54, a right ventricular (RV) shocking terminal (coil) 56, and an SVC shocking terminal (coil) 58, which are adapted for connection to the right ventricular tip electrode 32, right ventricular ring electrode 34, the right ventricle coil electrode 36, and the SVC coil electrode 38, respectively.

At the core of the stimulation device 10 is a programmable microcontroller 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry.

Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art. Representative types of control circuitry that may be used with the present invention include the microprocessor-based control system of U.S. Pat. No. 4,940,052 (Mann et al.), and the state-machine of U.S. Pat. No. 4,712,555 (Sholder) and U.S. Pat. No. 4,944,298 (Sholder).

As shown in FIG. 2, an atrial pulse generator 70 and a ventricular pulse generator 72 generate stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g. pacing rate, atrio-ventricular (AV) delay, atrial inter conduction (A-A) delay, or ventricular inter conduction (V-V) delay, etc.), as well as to keep track of the timing of refractory periods, PVARP intervals, noise detection windows, evoked response windows, alert intervals, marker channel timing, etc.

The switch bank 74 includes a plurality of switches for connecting the desired electrodes to the appropriate I/O circuits, thereby providing complete electrode programmability. Accordingly, the switch bank 74. in response to a control signal 80 from the microcontroller 60, determines the polarity of the stimulation pulses (e.g. unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity. In accordance with the present invention, the polarity for sensing the ventricular EGM during capture verification and the polarity for sensing the atrial EGM during fusion detection can be programmably selected.

Each of the atrial sensing circuit 82 or the ventricular sensing circuit 84 preferably employs one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. For a complete description of a typical sensing circuit, refer to U.S. Pat. No. 5,573,550, titled "Implantable Stimulation Device having a Low Noise, Low Power, Precision Amplifier for Amplifying Cardiac Signals" (Zadeh et al.). For a complete description of an automatic gain control system, refer to U.S. Pat. No. 5,685, 315, titled "Cardiac Arrhythmia Detection System for an Implantable Stimulation Device" (McClure et al.). The patents (U.S. Pat. Nos. 5,573,550 and 5,685,315) are hereby incorporated herein by reference. The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart.

The atrial and ventricular sensing circuits 82 and 84, in turn, receive control signals over signal lines 86 and 88 from the microcontroller 60, for controlling the gain, threshold, polarization charge removal circuitry (not shown), and the timing of any blocking circuitry (not shown) coupled to the inputs of the atrial and ventricular sensing circuits 82 and 84.

For arrhythmia detection, the stimulation device 10 utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing circuitry within the microcontroller 60, and enabling the data acquisition system 90 via control signal 92 to sample the cardiac signal that falls in the capture detection window and, based on the amplitude of the sampled cardiac signal, determines if capture has occurred. In accordance with a preferred embodiment of the present invention, whenever capture verification is enabled, the methods for distinguishing loss of capture from fusion as described herein are employed.

If a loss of capture in any chamber is detected during capture verification, microcontroller 60 initiates a threshold test to redetermine the capture threshold in that particular chamber. In one embodiment, a capture threshold test may also be performed on a periodic basis, such as once a day during at least the acute phase (e.g. the first 30 days) and less frequently thereafter. A threshold test would begin at a desired starting point (either a high energy level or the level at which capture is currently occurring) and decrease the energy level until capture is lost. The value at which capture is lost is known as the capture threshold. Thereafter, the stimulation pulse energy is adjusted to the capture threshold plus some safety margin. The methods of the present invention for detecting and avoiding fusion may be applied during threshold testing such that stimulation output is not driven to a maximum level due to fusion events precluding capture recognition.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. Advantageously, the operating parameters of the stimulation device 10 may be non-invasively programmed into the memory 94 through a telemetry circuit 100 in telemetric communication with the external device 102, such as a programmer, trans-telephonic transceiver, or a diagnostic system analyzer.

The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

In one embodiment, the stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g. detecting sleep and wake states). Accordingly, the microcontroller 60 responds by adjusting the various stimulation parameters (such as rate, AV Delay, V-V Delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time and also be capable of providing high-current pulses (for capacitor charging) when the patient requires a shock pulse. The battery 110 must preferably have a predictable discharge characteristic so that elective replacement time can be detected. Accordingly, the stimulation device 10 can employ lithium/silver vanadium oxide batteries.

As further shown in FIG. 2, the stimulation device 10 is shown as having an impedance measuring circuit 112 which is enabled by the microcontroller 60 by a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; predicting the remaining battery life; measuring stroke volume; and detecting the opening of the valves, etc. The impedance measuring circuit 120 is advantageously coupled to the switch bank 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the left atrial coil electrode 28, the right ventricle coil electrode 36, and/or the SVC coil electrode 38 (FIG. 1). As noted above, the housing 40 may act as an active electrode in combination with the right ventricle electrode 36, or as part of a split electrical vector using the SVC coil electrode 38 or the left atrial coil electrode 28).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

It is thus seen that the present invention provides an implantable cardiac stimulation device capable of detecting fusion immediately when it occurs, without delivering additional stimulation pulses. Further, when fusion is detected, the present invention inhibits unnecessary back-up stimulation and threshold testing. Both of these features act to significantly conserve pacemaker battery expenditure. Additionally, by reliably detecting fusion, the present invention provides for adjustments to be made to stimulation parameters that will reduce the likelihood of fusion during future stimulation cycles. Furthermore, an implantable cardiac stimulation device possessing the means for detecting fusion, as set forth in the present invention, will obtain more reliable results from threshold tests by verifying that a failure to capture at a given pulse energy is not, in fact, fusion. Thus the present invention provides more reliable, effective stimulation therapy while conserving pacemaker battery energy and increasing the automation of the stimulation device.

While the invention herein disclosed has been described by means of specific embodiments and applications thereof, numerous modifications and variations could be made thereto by those skilled in the art without departing from the scope of the invention.

What is claimed is:

1. A method of detecting ventricular fusion events, the method comprising:
   delivering a ventricular stimulation pulse;
   monitoring a ventricular channel for an evoked response;
   monitoring an atrial channel for a far-field R-wave; and
   indicating a fusion event when an evoked response is not detected on the ventricular channel and the far-field R-wave is detected on the atrial channel.

2. The method according to claim 1, further comprising inhibiting delivery of a back-up stimulation pulse whenever the fusion event is indicated.

3. The method according to claim 1, further comprising indicating a loss of capture when an evoked response is not detected on the ventricular channel and a far-field R-wave is not detected on the atrial channel, and delivering a back-up stimulation pulse.

4. The method according to claim 1, further comprising automatically adjusting at least one stimulation parameter whenever the fusion event is indicated.

5. The method according to claim 4, wherein automatically adjusting at least one stimulation parameter comprises automatically adjusting at least one of an AV interval and a PV interval subsequent to an indication of the fusion event.

6. The method according to claim 4, wherein automatically adjusting at least one stimulation parameter comprises automatically adjusting a stimulation rate subsequent to an indication of the fusion event.

7. The method according to claim 1, wherein delivering comprises delivering the stimulation pulse in at least one of a right ventricular chamber or a left ventricular chamber.

8. The method according to claim 7, wherein detecting the far-field R-waves comprises analyzing an atrial intra-cardiac electrogram signal following the delivery of the ventricular stimulation pulse.

9. The method according to claim 8, further comprising:
detecting a ventricular evoked response on the ventricular channel based on a predetermined criteria; and
triggering the detection of the far-field R-wave on the atrial channel when the detected ventricular evoked response does not match the predetermined criteria.

10. The method according to claim 9, wherein indicating the fusion event comprises indicating that the far-field R-wave on the atrial channel substantially coincides in time with the detected ventricular evoked response that does not match the predetermined criteria.

11. A stimulation device for detecting a fusion event, the stimulation device comprising:
a pulse generator configured to generate a ventricular stimulation pulse;
ventricular sensing circuitry that is operative to monitor for an evoked response following delivery of the ventricular stimulation pulse;
atrial sensing circuitry that is operative to monitor for a far-field R-wave following delivery of the ventricular stimulation pulse; and
a controller connected to the atrial sensing circuitry and ventricular sensing circuitry, wherein the controller is configured to detect a fusion event when the evoked response is not detected and the far-field R-wave is detected.

12. The stimulation device according to claim 11, wherein the controller inhibits delivery of a back-up stimulation pulse if the fusion event is confirmed.

13. The stimulation device according to claim 12, wherein the controller causes the pulse generator to deliver a back-up stimulation pulse if the evoked response is not detected and the far-field R-wave is not detected.

14. The stimulation device according to claim 11, wherein the controller automatically adjusts one or more stimulation parameters if the fusion event is confirmed.

15. The stimulation device according to claim 11, wherein the controller performs capture verification in at least one of a right ventricular chamber and a left ventricular chamber.

16. The stimulation device according to claim 15, wherein the atrial sensing circuitry samples an atrial intra-cardiac electrogram signal following delivery of the ventricular stimulation pulse.

17. The stimulation device according to claim 11, wherein the ventricular sensing circuitry is operative to sample a ventricular intra-cardiac electrogram signal from the ventricular chamber in which the stimulation pulse is applied; and
wherein the controller performs ventricular evoked response verification by determining when an evoked response is detected from a sampled ventricular intra-cardiac electrogram signal.

18. The stimulation device according to claim 17, wherein the controller confirms the occurrence of the fusion event when a far-field R-wave substantially coincides in time with an evoked response on the ventricular channel that is below a predetermined threshold.

19. A method for detecting a fusion event, the method comprising:
delivering a stimulation pulse in a ventricular chamber;
following the delivered stimulation pulse, detecting a signal on a ventricular channel that does not satisfy a predetermined criteria associated with an evoked response signal;
following the delivered stimulation pulse, detecting one of an absence or a presence of a far-field R-wave on an atrial channel;
inhibiting delivery of a back-up stimulation pulse when the far-field R-wave is present; and
delivering a back-up stimulation pulse when the far-field R-wave is absent.

20. The method according to claim 19, wherein delivering comprises delivering the stimulation pulse in at least one of a right ventricular chamber or a left ventricular chamber.

21. The method according to claim 19, wherein detecting the absence or presence of the far-field R-waves comprises analyzing an atrial intra-cardiac electrogram signal following the delivery of the ventricular stimulation pulse.

22. The method according to claim 21, further comprising:
indicating a fusion event when the far-field R-wave on the atrial channel substantially coincides in time with the detected ventricular evoked response that does not meet the predetermined criteria.

* * * * *